(12) United States Patent
Arai (10) Patent No.: US 6,573,712 B2
(45) Date of Patent: Jun. 3, 2003

(54) NON-DESTRUCTIVE INSPECTION DEVICE (75) Inventor: Makoto Arai, Kanagawa (JP)

(73) Assignee: NSK Ltd., Tokyo (JP)

( * ) Notice: Subject to any disclaimer, the term of this patent is extended or adjusted under 35 U.S.C. 154(b) by 0 days.

(21) Appl. No.: 09/739,650

(22) Filed: Dec. 20, 2000

(65) Prior Publication Data

US 2001/0017540 A1 Aug. 30, 2001

(30) Foreign Application Priority Data

Dec. 20, 1999 (JP) ............................................. 11-361075

(51) Int. Cl.$^7$ .......................... G01N 27/90; G01N 27/72
(52) U.S. Cl. ........................ 324/238; 324/240; 324/225; 702/38
(58) Field of Search ..................... 324/207.12, 207.15, 324/209, 207.26, 228, 243, 238, 240, 225; 702/38

(56) References Cited

U.S. PATENT DOCUMENTS 4,675,604 A * 6/1987 Moyer et al. ............... 324/220
4,727,322 A * 2/1988 Lonchampt et al. ......... 324/229
4,755,753 A * 7/1988 Chern .......................... 324/237
5,111,142 A * 5/1992 Mazzone et al. ......... 324/207.23
5,291,136 A * 3/1994 Van der Veer et al. ...... 324/262
5,371,461 A * 12/1994 Hedengren .................. 324/225
5,424,640 A * 6/1995 Levy ........................... 324/232
5,541,510 A * 7/1996 Danielson .............. 324/207.16
5,698,977 A * 12/1997 Simpson et al. ............ 324/209
5,854,553 A * 12/1998 Barclay et al. ......... 324/207.16

* cited by examiner

*Primary Examiner*—Edward Lefkowitz
*Assistant Examiner*—Darrell D Kinder
(74) *Attorney, Agent, or Firm*—Sughrue Mion, PLLC (57) ABSTRACT In a non-destructive inspection device of the present invention which detects in a non-destructive manner a defect of a member to be inspected, based on a change in magnetic fluxes due to eddy currents that are generated by an inspection probe having a coil, a driving section which adjusts a position of the inspection probe, and measuring device for, based on a detection signal of the inspection probe, measuring a lift-off between the inspection probe and the member to be inspected are disposed. The driving section is controlled in accordance with a result of measurement of the measuring device, whereby a control of making the lift-off constant is performed.

20 Claims, 6 Drawing Sheets

NON-DESTRUCTIVE INSPECTION DEVICE

BACKGROUND OF THE INVENTION

1. Field of the Invention

The present invention relates to a non-destructive inspection device in which, when a defect of a member to be inspected (hereinafter, such a member is often referred to as inspection member) having a complex shape configured by combining planar and curved faces with one another is inspected in a non-destructive manner, the distance (lift-off) between an inspection probe and the inspection member is controlled to be always constant, thereby improving the inspection accuracy.

2. Description of the Related Art

As the advancement of downsizing and performance of a mechanical structure or a device, a stress which is applied as a load to a structure is increasing. Therefore, even when a defect is small from the viewpoint of a field of a material strength, stress concentration produces a large influence. As a result, it is requested to surely detect even a small defect (impact mark, crack, damage, grinding burn, or the like).

Figure 5:
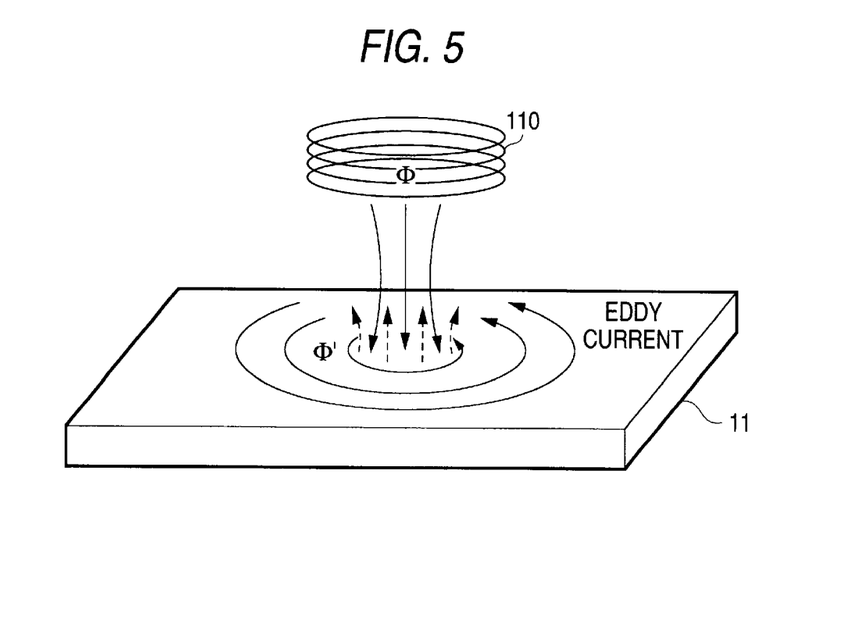
FIG. 5 is a diagram showing the principle of a non-destructive inspection device used in the invention.
Figure 6:
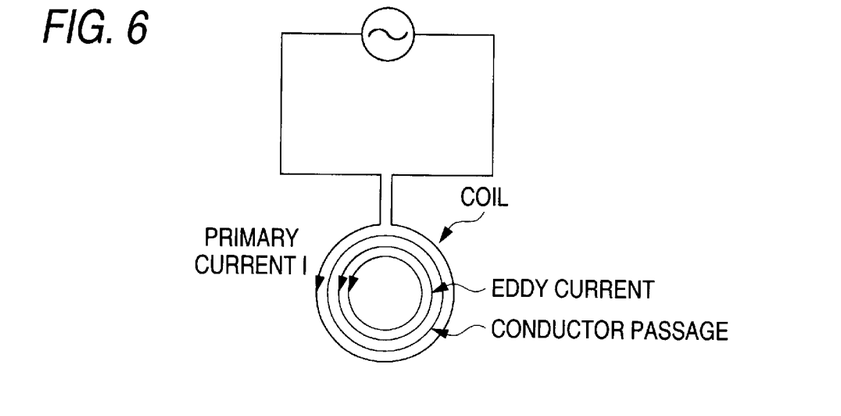
FIG. 6 is a diagram showing a distribution of eddy currents in the case where there is no defect.
Figure 7:
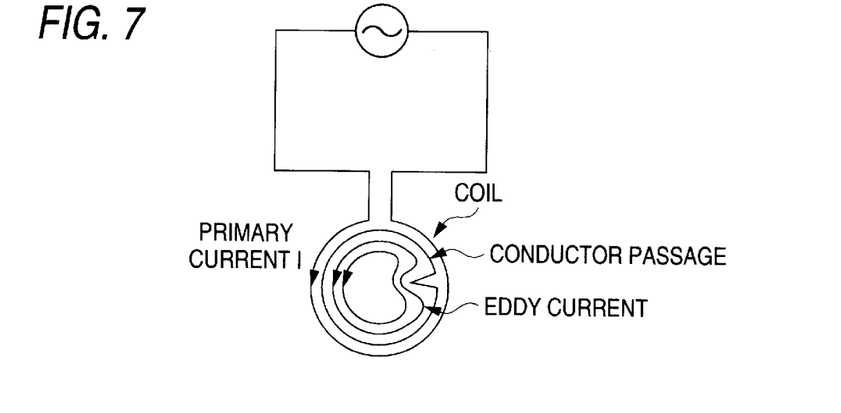
FIG. 7 is a diagram showing a distribution of eddy currents in the case where there is a defect.

Conventionally, a device shown FIG. 5 is known as a defect inspection device which satisfies such a requirement. In the device, an AC current is supplied to a coil 110 to induce eddy currents in an inspection member 11 which is opposed to the coil. A defect is detected in a non-destructive manner on the basis of a phenomenon in which the amplitude and phase of the eddy currents are changed depending on the dimensions, kinds of the defect, the permeability, the conductivity, and the like of the inspection member 11, i.e., a change of an impedance of the coil 110. In FIG. 5, $\phi'$ indicates magnetic fluxes generated by the eddy currents. FIG. 6 is a diagram of eddy currents in the case where the inspection member 11 has no defect. By contrast, in the case where the inspection member 11 has a defect, i.e., the case where a passage of a conductor is bent to change its shape as shown in FIG. 7, also eddy currents are changed in accordance with the change, so that the defect of the inspection member 11 is inspected in a non-destructive manner.

Figure 8:
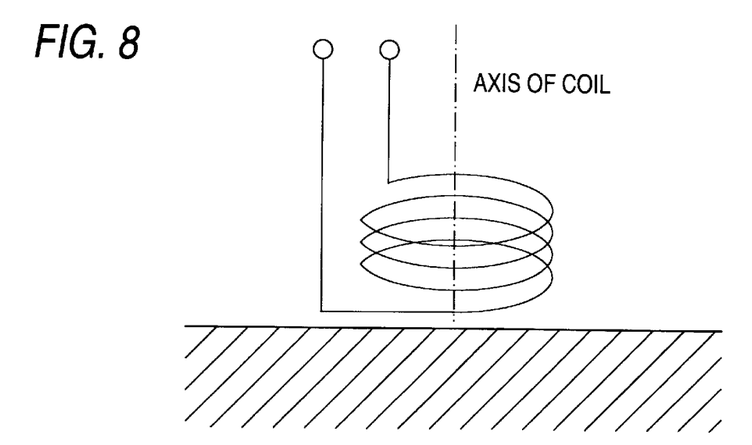
FIG. 8 is a view showing the manner of winding a coil in the case where an output of an absolute value signal is to be obtained.

It is known that, when the coil 110 is wound into the absolute type as shown in FIG. 8, such a defect inspection device based on eddy currents is suitably used for detecting changes in all of the dimensions, kinds of the defect, the magnetic permeability, the conductivity, and the like. It is known also that, when two coils are wound in the differential type, a crack can be detected more sensitively.

An inspection member which is to be inspected by such a non-destructive inspection device often has a complex shape configured by combining planar and curved faces with one another. When an inspection member having such a complex shape is to be inspected, a moving mechanism having degrees of freedom in three or more axes is used, and inspection is performed while tracing the shape of the inspection member by interpolating the three axes. In a method of the conventional art, coordinates of an inspection probe for scanning the inspection member are preset, and inspection is performed in accordance with the preset coordinates.

Therefore, the distance (lift-off) between the inspection probe and the inspection member is affected by, for example, setting errors of the inspection probe and the inspection member, and the tolerance of the inspection member, and hence the lift-off is varied. When the lift-off is changed by scanning of the inspection probe, setting errors of the inspection probe and the inspection member, the tolerance of the inspection member, and the like, eddy currents in the inspection member due to magnetic fluxes generated by the coil in the inspection probe is changed, so that the impedance of the coil in the inspection probe is largely changed. The impedance change of the coil in the inspection probe is larger than that due to a defect to be detected. When the lift-off is varied, therefore, there arises a problem in that the detection accuracy of the inspection is not stable.

Figure 2:
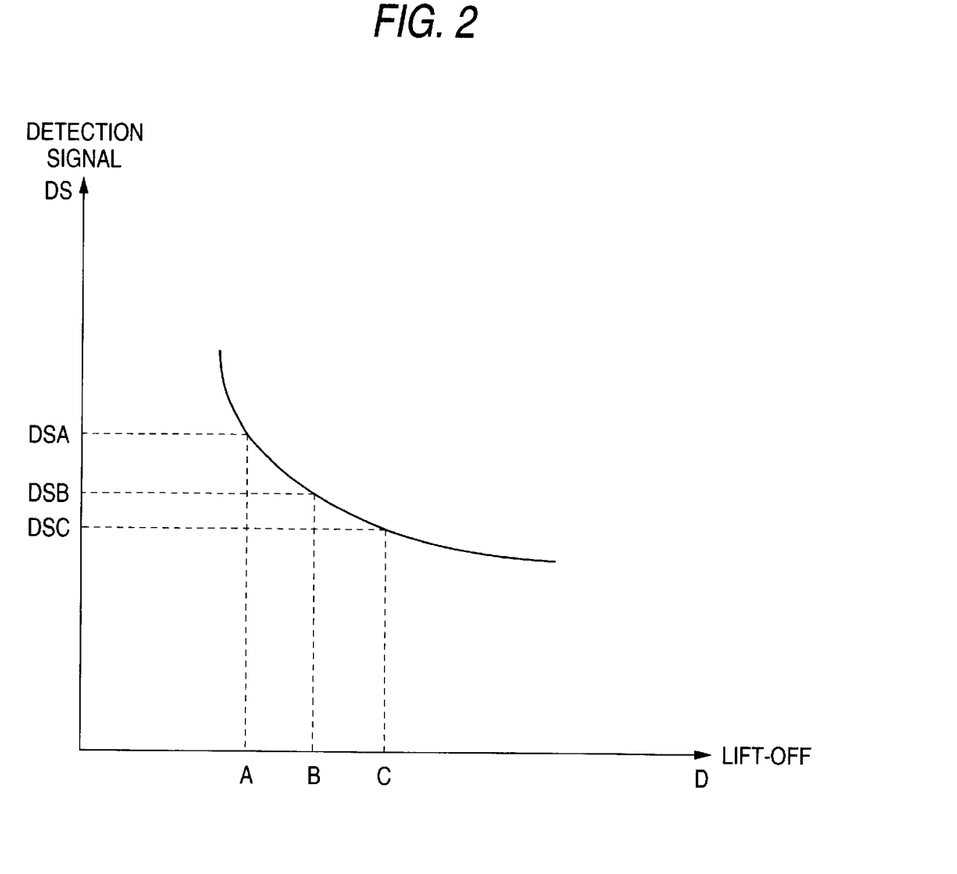
FIG. 2 is a view showing an example of characteristics of an inspection probe used in the invention.

When inspection using an inspection probe is performed while setting based on design values is unchanged, a dimension difference of several tens of p.m is caused in the lift-off by the tolerance error of the workpiece, the error in chucking of the inspection member, the error in setting of the inspection member, and the like. An output signal of a non-destructive inspection device has relationships such as shown in FIG. 2 with the lift-off. When the lift-off is changed, therefore, also the level of the output signal is largely changed.

Figure 9:
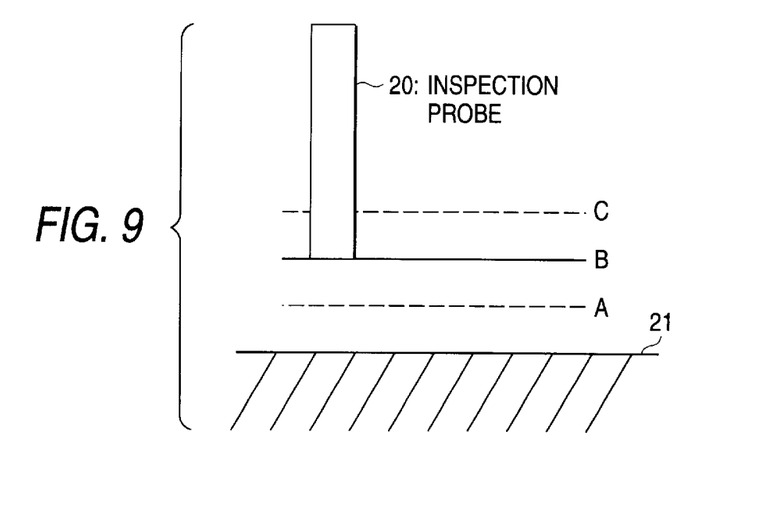
FIG. 9 is a view showing relationships between an inspection probe and an inspection member.
Figure 10:
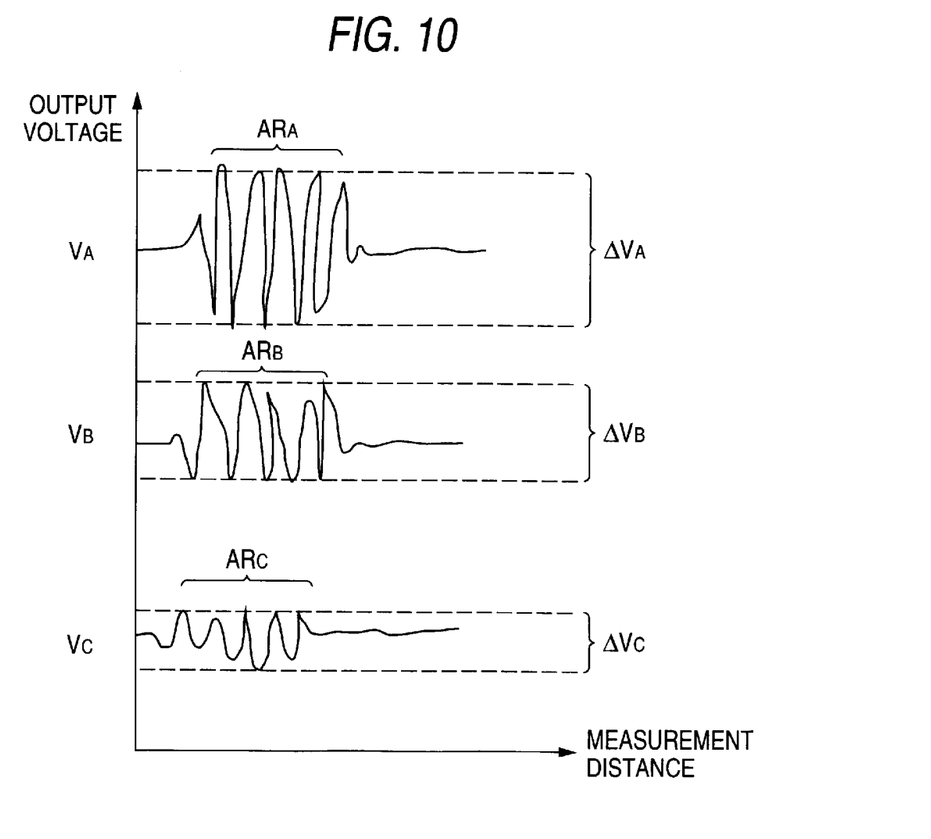
FIG. 10 is a waveform chart showing examples of a defect detection signal and relationships of detection signals corresponding to the lift-off between an inspection probe and an inspection member.

FIGS. 9 and 10 show relationships between the lift-off and the detection signal, and the state of a defect in the detection signal. When inspection is performed with placing an inspection probe 20 in position A (too close), B (normal), or C (too remote) with respect to an inspection member 21, the level of the detection signal (output voltage) V is changed as indicated by $V_A$, $V_B$ or $V_C$. Namely, as the lift-off is larger, the level of the output voltage V is lower, and, as the lift-off is smaller, the level of the output voltage V is higher. An inspection area $AR_A$ of the output voltage $V_A$ shows a signal corresponding to a defect, an area inspection $AR_B$ of the output voltage $V_B$ shows a signal corresponding to the defect, an inspection area $AR_C$ of the output voltage $V_C$ shows a signal corresponding to the defect, and $\Delta V_A$, $\Delta V_B$, and $\Delta V_C$ show the levels of the signals corresponding to same defect, respectively.

Conventionally, in an inspection member, the requested accuracy of the size of a defect is not very high. Even when the absolute value of the output signal is somewhat varied in degree, therefore, a defect can be detected because the level difference between outputs from a defect detection section are large. By contrast, with respect to a small defect, the output signal is low in level. When the lift-off is large and the level of the output signal is low, therefore, the output signal is buried in noises and cannot be detected. When $V_B > V_C$ and $\Delta V_B > \Delta V_C$ in FIG. 10, for example, it is impossible to judge which defect is larger.

On the other hand, when the distance between the inspection probe and the inspection member is too small, there is a fear that the probe may be in contact with the member. Usually, as the surface area where an inspection probe is opposed to an inspection member is larger, the detection accuracy is higher, and an output of a sufficient level cannot be obtained unless the probe and the member are somewhat closer. In the case where an inspection member having a complex shape configured by combining a planar face (straight line) and a curved face (curved line) with one another, a concave curved or spherical face, a cylindrical face, or the like is to be inspected, when an inspection probe is planar or larger in radius of curvature than the inspection member, therefore, a state may be caused in which the inspection probe is made excessively closer to the inspection member to be in contact therewith.

In such a non-destructive inspection device, usually, defect judging means makes a judgement in either of the following manners: (1) if the difference between a detection signal obtained from an inspection member with respect to a reference level is larger than a predetermined value, the inspection member is judged failure; and (2) if the difference between a detection signal with respect to a reference level is smaller than a constant value (for example, 20%), the inspection member is judged acceptable, and, if not, the inspection member is judged failure. However, such means has a problem as follows. In (1) above, when the probe position is excessively remote as in the case of position C shown in FIG. 9 and the signal level is low, the inspection member is judged acceptable in spite of failure. By contrast, in (2), the inspection member is judged failure not only when the probe position is excessively remote as in the case of position C with the output level is low, but also when the probe position is excessively close as in the case of position A with the output is high.

SUMMARY OF THE INVENTION

The invention has been conducted under the above-mentioned circumstances. It is an object of the invention to provide a non-destructive inspection device in which inspection can be stabilized by correcting a change of the lift-off due to setting errors of an inspection probe and an inspection member, or the tolerance of the inspection member, the time period required for the correction can be minimized so as to suppress an increase of the inspection time period, and an influence of the change of the lift-off can be minimized without adding a distance sensor or the like.

The invention relates to a non-destructive inspection device which detects in a non-destructive manner a defect of a member to be inspected, based on a change in magnetic fluxes due to eddy currents that are generated by an inspection probe having a coil. The object of the invention can be attained by comprising: a driving section which adjusts a position of the inspection probe; and measuring device for, based on a detection signal of the inspection probe, measuring a lift-off between the inspection probe and the member to be inspected, and controlling the driving section in accordance with a result of measurement of the measuring device, whereby a control of making the lift-off constant is enabled.

The object of the invention can be attained more effectively by winding the coil into the absolute type, and outputting a detection signal of the inspection probe as an absolute value, or by configuring the coil as two coils which are wound in the differential type.

DETAILED DESCRIPTION OF THE PREFERRED EMBODIMENT

In the non-destructive inspection device of the invention, an absolute value signal of an output of the inspection probe which is used for detecting a defect such as an impact mark, a crack, or the like is employed, an absolute value signal component of a detection signal from the inspection probe is used as means for measuring the distance (lift-off) between the inspection probe and the inspection member, and the position of the inspection probe is feedback-processed on the basis of a result of the measurement of the lift-off to adjust the position. According to this configuration, the inspection can be performed while always maintaining the lift-off constant, and hence it is possible to realize highly accurate non-destructive inspection. Since the position of the inspection probe can be adjusted without adding a position sensor, the size of the device is not increased.

Hereinafter, an embodiment of the invention will be described with reference to the accompanying drawings.

Figure 1:
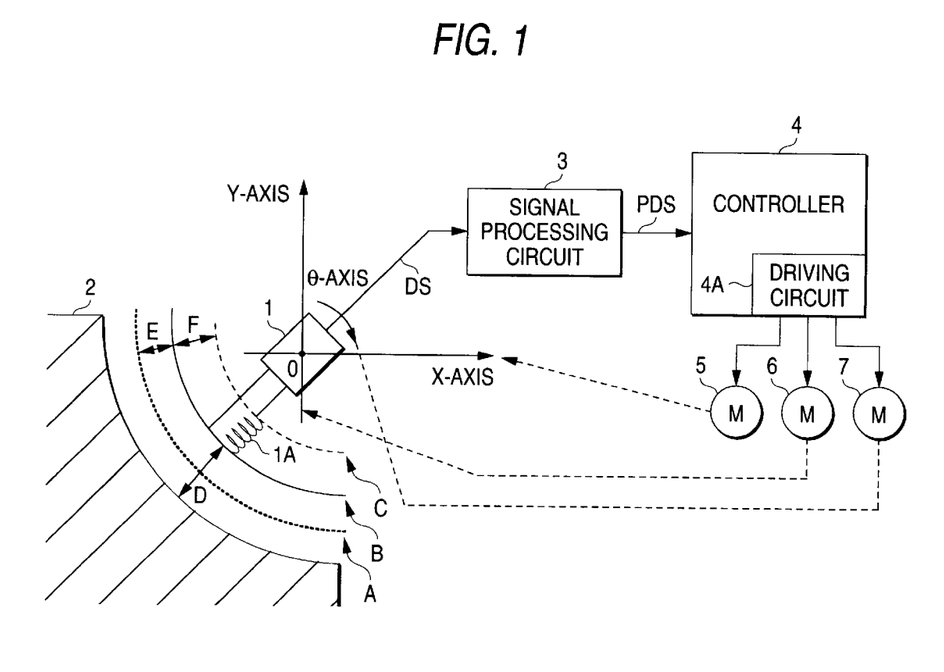
FIG. 1 is a diagram showing an embodiment of the invention.

FIG. 1 shows an embodiment of the invention. An inspection coil 1A of an inspection probe 1 which is moved in the X- and Y-axis directions and rotated about the θ-axis is set so as to be opposed to the surface of an inspection member 2 with being separated therefrom by a distance D (for example, 100 to 1,000 μm, preferably, 100 to 500 μm). An orbit B indicated by the solid line is a target orbit which is to be traced by the coil in order to inspect the surface of the inspection member 2. Orbits which are indicated by broken lines and deviated from the target orbit B by a distance E or F are indicated by A and C, respectively. The distance E or F is a setting error, a process error, or the like, and usually exists in the range of about ±100 μm. A detection signal DS of the inspection probe 1 is supplied to a signal processing circuit 3 to be sequentially subjected to processes such as signal amplification, A/D conversion, calculation of deviation amounts of the coordinates, and calculation of the amount of interpolation using an interpolation coordinate table. An interpolation signal PDS of the detection signal is supplied to a controller 4 configured by a CPU, etc. Motors 5 to 7 are connected to the controller 4 via a driving circuit 4A. The motor 5 drives the X-axis, the motor 6 drives the Y-axis, and the motor 7 drives the θ-axis. A feedback control of the position of the inspection probe 1 is performed by driving the X- and Y-axes by means of the motors 5 and 6. In the embodiment, the position of the inspection probe 1 is adjusted in the X- and Y-axes. Alternatively, the position may be adjusted in three axes in which the Z-axis is added to the X- and Y-axes.

Conventionally, calculation is performed on the basis of the shape and dimensions of the inspection member 2, and the shape, dimensions, and locus of the inspection probe 1 to determine the center of setting of the inspection probe 1 to position 0 (origin) of FIG. 1, and measurement is then performed. By contrast, in the invention, before measurement, the distance (lift-off) between the inspection probe 1 and the inspection member 2 is measured in plural positions along the locus to be measured, and it is checked whether or not the center position 0 is within an allowable range of the lift-off (locus B) to be measured. If the lift-off is deviated from the locus B, a feedback control is performed until the lift-off enters a given range with respect to the locus B. Then, inspection is performed while setting the inspection probe 1 to be moved along the locus B.

The relationship between the detection signal DS (or the signal PDS), and the lift-off D between the tip end of the inspection probe 1 and the inspection member 2 is indicated by an inverse-proportion curve such as shown in FIG. 2. Therefore, the distance D can be detected from the level of the detection signal DS (or the signal PDS). In FIG. 2, the detection signal DS of the locus A in which the lift-off D is close to the inspection member 2 has a larger value $DS_A$, the detection signal DS of the locus B has a value $DS_B$, and the detection signal DS of the locus C which is remote from the inspection member 2 has a smaller value $DS_C$. As the lift-off D is larger, the detection signal DS is smaller in level.

In FIG. 1, the orbit A is closer than the target orbit B which is to be traced, and the orbit C is remoter than the target orbit B. From the relationships shown in FIG. 2, deviation amounts E and F from the target orbit B are obtained on the basis of the level of the detection signal DS. Interpolation data are obtained from the interpolation coordinate table on the basis of the deviation amounts E and F. A feedback control is performed on the motors 5 and 6 based on the interpolation data, thereby correcting the position of the inspection probe 1 to the target orbit B (lift-off D) which is to be traced. This measurement of the lift-off serves also as acquisition of signals which are to be used in the defect inspection. Therefore, the position of the inspection probe 1 can be corrected without adding a distance sensor.

Figure 3:
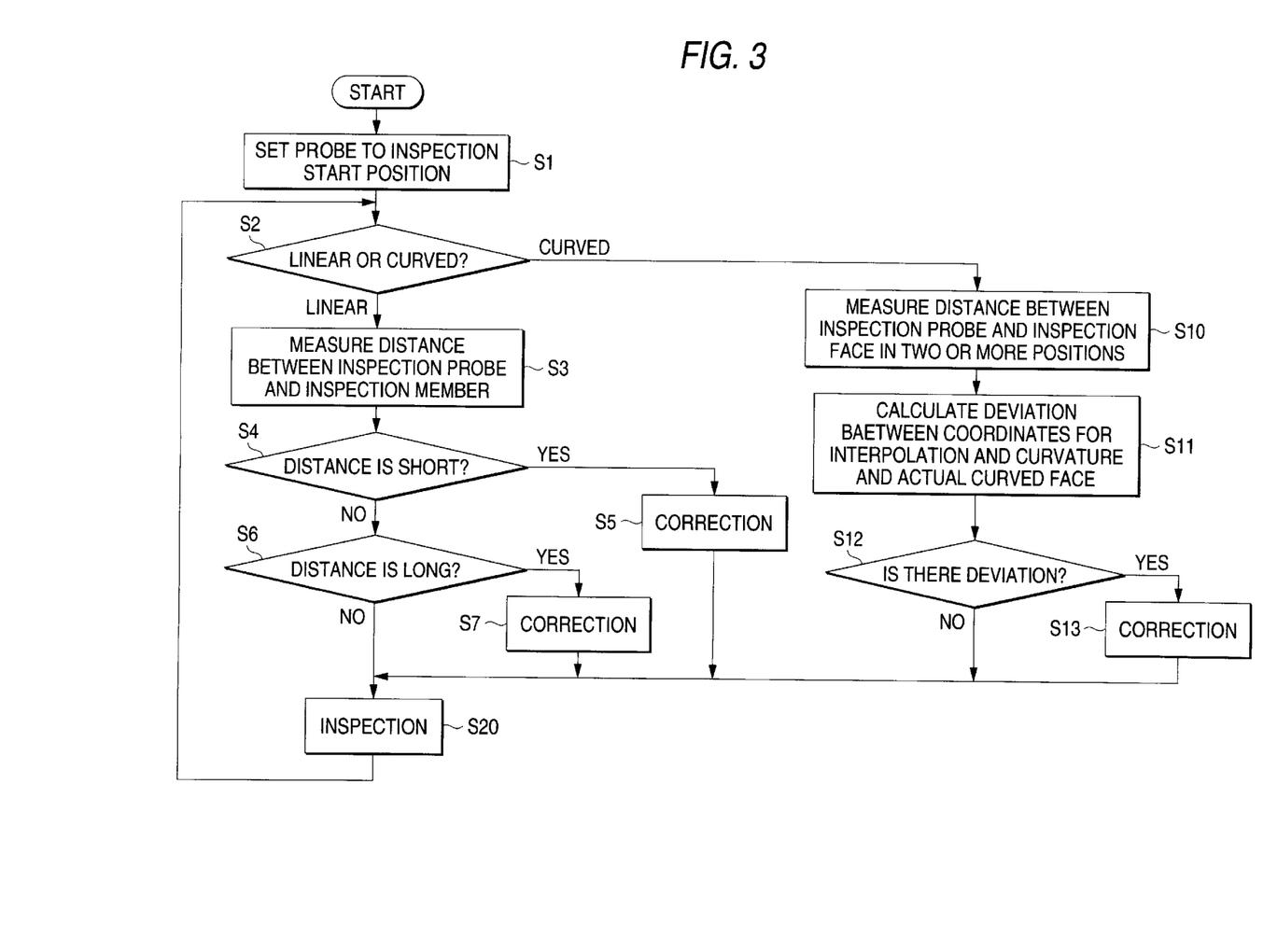
FIG. 3 is a flowchart showing an example of the operation of the invention.

FIG. 3 shows an example of the inspection operation in the invention. First, the inspection probe 1 is set to an inspection start position (step S1), and it is judged whether the inspection member 2 is linear or curved (step S2). If it is judged that the inspection member is linear, the lift-off D which is the distance between the inspection probe 1 and the inspection member 2 is measured by the method that has been described with reference to FIG. 2 (step S3). It is then judged whether or not the lift-off D is deviated toward E from the target orbit B which is to be traced, to be closer to the inspection member 2 (step S4). The measurement and judgements are performed by the controller 4. If the lift-off is closer to the inspection member 2, the motors 5 and 6 are driven by the controller 4 on the basis of the interpolation amount which is calculated by the signal processing circuit 3, thereby correcting the position (step S5). Thereafter, the defect inspection is performed while moving the inspection probe 1 (step S20).

If it is judged in step S4 that the lift-off D is not closer than the target orbit B which is to be traced, it is then judged whether or not the lift-off is deviated toward F from the target orbit B to be remoter from the inspection member 2 (step S6). If the lift-off is remoter from the inspection member, the motors 5 and 6 are driven by the controller 4 on the basis of the interpolation amount which is calculated by the signal processing circuit 3, thereby correcting the position (step S7). Thereafter, the defect inspection is performed while moving the inspection probe 1 (step S20).

By contrast, if it is judged in step S2 that the inspection member 2 is curved, the lift-off D which is the distance between the inspection probe 1 and the inspection member 2 is measured in two or more positions (step S10). From a result of the measurement, a deviation between coordinates for interpolation or the curvature, and the actual curved face is calculated (step S11), and it is then judged whether there is a deviation or not (step S12). If there is no deviation, the inspection is performed without performing correction (step S20). If there is a deviation, the motors 5 and 6 are driven in the same manner as described above to perform correction (step S13), and the defect inspection is then performed while moving the inspection probe 1.

The non-destructive inspection device of the invention implements the defect inspection while repeating the above-mentioned operations. Alternatively, the lift-off may be adjusted before the defect inspection, and the defect inspection may be then performed.

When correction of the radius is relatively small with respect to the design value, the center position O of the XY coordinates can be determined by performing the measurement in at least two positions. Correction of the radius is enabled by performing the measurement in three or more positions.

Figure 4:
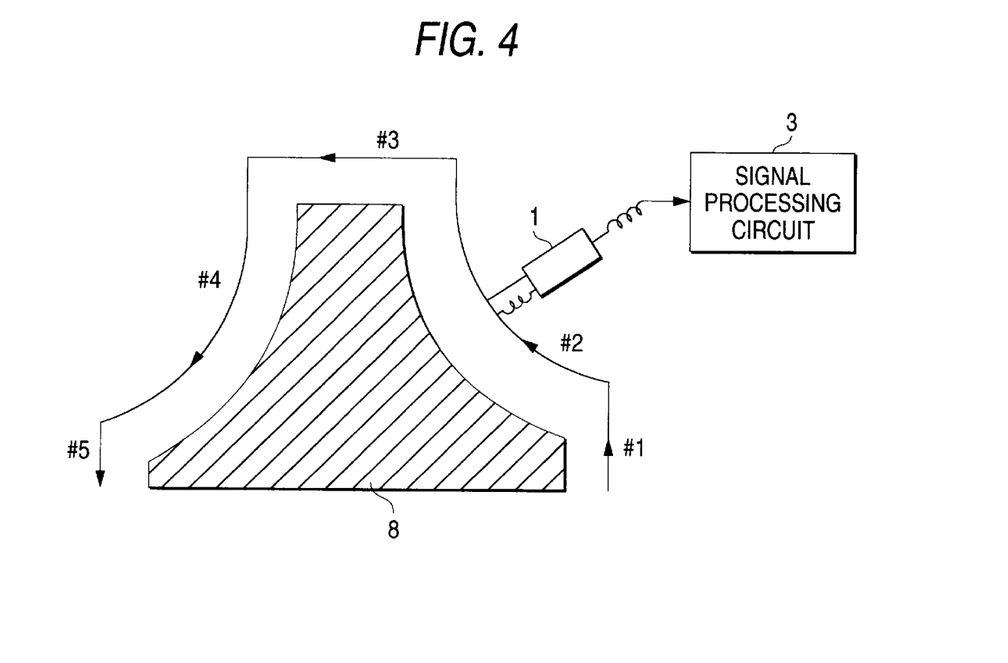
FIG. 4 is a diagram showing a manner of inspecting a component of a disk of a continuously variable transmission.

In the case where the shape of a trapezoid-like inspection member (a disk of a continuously variable transmission) 8 such as shown in FIG. 4 is to be inspected, inspection is continuously performed in the sequence of an end face (locus #1) → a spherical face (locus #2) → an upper end face (locus #3) → a spherical face (locus #4) → an end face (locus #5). Also in this case, the lift-off which is the distance from the inspection face is previously measured, identification is conducted so that movement of the inspection probe is continuously constant, and the inspection probe is moved along the locus, whereby inspection can be accurately performed.

FIG. 4 shows an example in which the invention is applied to a disk of a continuously variable transmission. The invention is effective also in a defect inspection of the surface of a complex shape in which strength must be ensured, such as a hub unit of an automobile, a raceway surface of a constant-velocity joint, a contact surface of a universal joint, a spherical roller bearing, a bearing with a shaft, a grooving surface of a ball screw, or a guiding surface of a linear guide.

As described above, according to the non-destructive inspection device of the invention, since the detection signal from the inspection probe is used also as means for detecting the lift-off between the inspection probe and the inspection member, the lift-off can be controlled to be constant without newly disposing a distance (lift-off) sensor, whereby the accuracy of inspection can be improved and inspection can be stably performed. Since a special additional device is not required, the performance of the device can be improved while maintaining the present production cost.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A non-destructive inspection device for detecting a defect of a member to be inspected, comprising:
   an inspection probe which is opposed to a surface of said member to be inspected, detects said defect and outputs a detection signal;
   a controller which inputs said detection signal from said inspection probe and measures a lift-off between said inspection probe and said member to be inspected on the basis of a change in magnetic fluxes of eddy currents due to said inspection probe, said controller comprising means for detecting whether said surface is linear or curved; and a driving unit which adjusts a position of said inspection probe relative to said surface of said member to be inspected so that said inspection probe performs a sequence of measurements as it is moved along a locus of points adjacent to said surface, wherein
if said controller determines that said surface is linear, said controller:
measures a lift-off distance between said inspection probe and said surface; and
determines whether said measured lift-off distance is within a predetermined range of a target orbit and, if so, performs an inspection operation, wherein if said controller determines that said measured lift-off distance is not within said predetermined range, then said controller causes said driving unit to move said inspection probe with respect to said surface by an interpolation amount based on said measured lift-off distance and then performs an inspection; and
if said controller determines that said surface is curved, said controller:
measures a lift-off distance between said inspection probe and said surface at two or more points of said surface;
calculates whether there is a deviation between said measured lift-off distances at said two or more points and, if not, then performs an inspection operation, wherein if said controller calculates that there is a deviation, then said controller causes said driving device to move said inspection probe with respect to said surface by an interpolation amount based on said measured lift-off distances and then performs an inspection.

2. The non-destructive inspection device according to claim 1, wherein said driving unit is configured and arranged so as to control said lift-off to be constant on the basis of an output signal of said controller.

3. The non-destructive inspection device according to claim 2, wherein said inspection probe comprises a coil which is wound into an absolution-type, said inspection probe outputs an absolution signal to said controller.

4. The non-destructive inspection device according to claim 1, said non-destructive inspection is applied to one selected from a group of a disk of a continuously variable transmission, a power roller, a hub unit of an automobile, a raceway surface of a constant-velocity joint, a contact surface of a universal joint, a spherical roller bearing, a bearing with a shaft, a grooving surface of a ball screw, and a guiding surface of a linear guide.

5. The non-destructive inspection device according to claim 2, wherein said controller controls said position of said inspection probe by a feedback control.

6. The non-destructive inspection device according to claim 5, wherein said driving unit comprises a motor and drives said motor for said feedback control on the basis of said output signal from said controller.

7. The non-destructive inspection device according to claim 2, wherein said inspection probe measures said lift-off prior to detecting said defect.

8. The non-destructive inspection device according to claim 7, wherein said inspection probe corrects a deviation amount of said position of said inspection probe with respect to a predetermined locus to place said position in a predetermined range.

9. The non-destructive inspection device according to claim 1, wherein said surface of said member to be inspected comprises a flat surface and a curved surface disposed adjacent to said flat surface.

10. The non-destructive inspection device according to claim 1, wherein said driving unit is configured and arranged to move said inspection probe with three degrees of freedom with respect to said surface of said member to be inspected.

11. The non-destructive inspection device according to claim 10, wherein said three degrees of freedom comprise linear movement along an x-axis direction, linear movement along a y-axis direction, and rotational movement in a θ-axis direction.

12. The non-destructive inspection device according to claim 2, wherein said driving unit maintains said lift-off in the range of from 100–1000 $\mu$m.

13. A non-destructive inspection device for detecting a defect of a member to be inspected, comprising:
an inspection probe which is opposed to a surface of said member to be inspected, detects said defect and outputs a detection signal, wherein said inspection probe comprises at least two coils which are respectively wound into a differential type; and
a controller which inputs said detection signal from said inspection probe and measures a lift-off between said inspection probe and said member to be inspected on the basis of a change in magnetic fluxes of eddy currents due to said inspection probe, said controller comprising means for detecting whether said surface is linear or curved, wherein
if said controller determines that said surface is linear, said controller:
measures a lift-off distance between said inspection probe and said surface; and
determines whether said measured lift-off distance is within a predetermined range of a target orbit and, if so, performs an inspection operation, wherein if said controller determines that said measured lift-off distance is not within said predetermined range, then said controller moves said inspection probe with respect to said surface by an interpolation amount based on said measured lift-off distance and then performs an inspection; and
if said controller determines that said surface is curved, said controller:
measures a lift-off distance between said inspection probe and said surface at two or more points of said surface;
calculates whether there is a deviation between said measured lift-off distances at said two or more points and, if not, then performs an inspection operation, wherein if said controller calculates that there is a deviation, then said controller moves said inspection probe with respect to said surface by an interpolation amount based on said measured lift-off distances and then performs an inspection.

14. The non-destructive inspection device according to claim 13, further comprising a driving unit which adjusts a position of said inspection probe and controls said lift-off to be constant on the basis of an output signal of said controller.

15. A non-destructive inspection method comprising:
setting a non-destructive inspection device to a starting position opposed to a surface of a member to be inspected, wherein said inspection device comprises:
an inspection probe which is opposed to a surface of said member to be inspected, detects said defect and outputs a detection signal;
a controller which inputs said detection signal from said inspection probe and measures a lift-off between said inspection probe and said member to be inspected on the basis of a change in magnetic fluxes of eddy currents due to said inspection probe; and a driving unit which adjusts a position of said inspection probe relative to said surface of said member to be inspected so that said inspection probe performs a sequence of measurements as it is moved along a locus of points adjacent to said surface;

detecting whether said surface is linear or curved;

if said surface is determined to be linear, said method further comprising:

measuring a lift-off distance between said inspection device and said surface;

determining whether said measured lift-off distance is within a predetermined range of a target orbit and, if so, performing an inspection operation, wherein if said measured lift-off distance is not within said predetermined range, then said method comprises moving said inspection device with respect to said surface by an interpolation amount based on said measured lift-off distance and then performing an inspection;

if said surface is determined to be curved, said method further comprises:

measuring a lift-off distance between said inspection device and said surface at two or more points of said surface;

calculating whether there is a deviation between said measured lift-off distances at said two or more points and, if not, then performing an inspection operation, wherein if there is a deviation, then said method comprises moving said inspection device with respect to said surface by an interpolation amount based on said measured lift-off distances and then performing an inspection.

16. The non-destructive inspection method according to claim 15, wherein said performing an inspection further comprises moving said inspection probe relative to said surface so that said inspection probe performs a sequence of measurements as it is moved along a locus of points adjacent to said surface.

17. The non-destructive inspection method according to claim 16, wherein said performing an inspection further comprises maintaining said lift-off distance constant as said inspection probe is moved along said locus of points adjacent to of said surface.

18. A non-destructive inspection method comprising:

setting a non-destructive inspection device to a starting position opposed to a surface of a member to be inspected;

detecting whether said surface is linear or curved;

if said surface is determined to be linear, said method further comprising:

measuring a lift-off distance between said inspection device and said surface;

determining whether said measured lift-off distance is within a predetermined range of a target orbit and, if so, performing an inspection operation, wherein if said measured lift-off distance is not within said predetermined range, then said method comprises moving said inspection device with respect to said surface by an interpolation amount based on said measured lift-off distance and then performing an inspection;

if said surface is determined to be curved, said method further comprises:

measuring a lift-off distance between said inspection device and said surface at two or more points of said surface;

calculating whether there is a deviation between said measured lift-off distances at said two or more points and, if not, then performing an inspection operation, wherein if there is a deviation, then said method comprises moving said inspection device with respect to said surface by an interpolation amount based on said measured lift-off distances and then performing an inspection.

19. The non-destructive inspection method according to claim 18, wherein said performing an inspection further comprises moving said inspection probe relative to said surface so that said inspection probe performs a sequence of measurements as it is moved along a locus of points adjacent to said surface.

20. The non-destructive inspection method according to claim 19, wherein said performing an inspection further comprises maintaining said lift-off distance constant as said inspection probe is moved along said locus of points adjacent to said surface.

* * * * *